United States Patent [19]

Waters, Jr. et al.

[11] Patent Number: 4,922,913
[45] Date of Patent: May 8, 1990

[54] INTRAOCULAR PRESSURE SENSOR

[76] Inventors: George E. Waters, Jr., R.R. 1, Westsfield, Ind. 46074; Robert L. Thommen, 2602 E. 58th St., Indianapolis, Ind. 46220

[21] Appl. No.: 119,087

[22] Filed: Nov. 12, 1987

[51] Int. Cl.$^5$ ............................................. A61B 3/16
[52] U.S. Cl. .................................................. 128/645
[58] Field of Search ..................... 128/645, 748, 635; 73/728

[56] References Cited

U.S. PATENT DOCUMENTS

| | | | |
|---|---|---|---|
| 3,542,589 | 7/1969 | Hargens et al. | 128/645 |
| 3,564,907 | 2/1971 | Holcomb et al. | 128/645 |
| 3,680,028 | 7/1972 | Black et al. | 128/645 X |
| 3,769,961 | 11/1973 | Fatt et al. | 128/635 |
| 3,893,444 | 7/1975 | Fatt | 128/635 |
| 4,089,329 | 5/1978 | Couvillon, Jr. et al. | 128/652 |
| 4,305,399 | 12/1981 | Beale | 128/645 |

OTHER PUBLICATIONS

Collins, "Miniature Passive Pressure Transducer", IEEE Trans. in Biomet. Eng., vol. BME 14, No. 2, 4/67.
Morey, "Contact Lens Tanometer", RCA TN No. 602, 12/64.

Primary Examiner—Max Hindenburg
Assistant Examiner—J. P. Lacyk
Attorney, Agent, or Firm—Fleit, Jacobson, Cohn, Price, Holman & Stern

[57] ABSTRACT

An intraocular pressure sensor utilizes a small sensitive piezo-resistance strain gauge cell mounted in a curved semi-rigid holder which serves to position the planar pressure sensitive surface of the strain gauge cell in contact with the eyeball surface. Deformation of the strain gauge cell due to contact with the eyeball produces an output signal corresponding to the intraocular pressure. The sensor is small and can be worn in the eye like a contact lens for extended periods of time permitting the intraocular pressures to be accurately monitored under normal living conditions, including during sleep. Fine wires are led from the sensor out over the eyelid for connection to an external recording/monitoring apparatus.

8 Claims, 1 Drawing Sheet

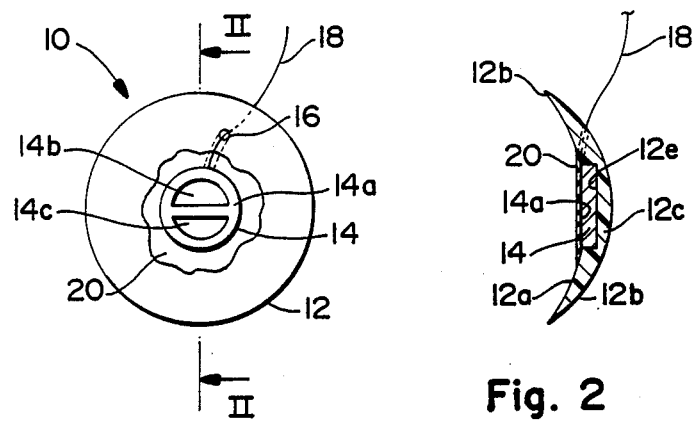
Fig. 1
Fig. 2
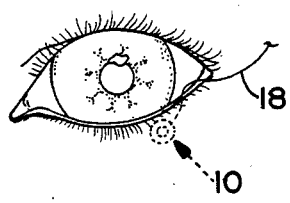
Fig. 3

INTRAOCULAR PRESSURE SENSOR

BACKGROUND AND SUMMARY OF THE INVENTION

The present invention relates to tonometry, the measurement of intraocular tension or pressure. More particularly, the present invention is concerned with a sensor means for use in tonometry for monitoring of intraocular pressure or tension.

Glaucoma is a disease in which the intraocular pressure is too high in a given eye. This elevated intraocular pressure produces a gradual loss of peripheral vision. Glaucoma is also characterized by hardening of the eyeball, and the disease, while leading to a gradual impairment of sight, can often result in blindness. There are a large number of people who are becoming visually impaired or going blind due to glaucoma, even with current diagnostic methods, modalities of treatment, the present level of knowledge and careful follow-up care.

It has been shown that some glaucoma victims had higher intraocular pressures than was originally thought, due to inaccuracy of current diagnostic methods which may not reliably evaluate the severity of a patient's condition. A current diagnostic method is to evaluate a patient's intraocular pressures on an intermittent basis, the intermittency being determined by a number of factors such as visual field defects, the health of the optic nerve, and the intraocular pressure levels. It has been shown from research testing that the intraocular pressure fluctuates widely and undergoes a diurnal variation. However, in general, most checking of a patient's intraocular pressure is done by the physician over a limited period of time between the hours of 8 a.m. to 10 p.m., which may not permit accurate monitoring of diurnal variations in the intraocular pressure.

Thus, for accurate assessment of a patient's intraocular pressure, the intraocular pressure level should be monitored over an extended period such as for 24 hours. Such extended monitoring, while highly desirable, is impractical due to the technical requirements of current testing methods and the fact that it would necessitate waking the patient every hour or every other hour as well as requiring the attendance of a physician. Consequently, intraocular pressure testing is generally not done during the period from 10 p.m. to 8 a.m., which period represents a significant portion of a patient's diurnal cycle. Furthermore, in the case that a patient's intraocular pressure is highest late at night or in the early morning hours, this would not be revealed by present testing methods.

The currently employed intraocular pressure testing devices and methods vary, but are based generally upon the well known principle that the pressure within a spherical body having a flexible surface, such as a balloon, can be measured by measuring the force required to deform the surface of the sphere. As applied to measuring intraocular pressure, this has been done in a number of ways.

The so-called "Shiotz tonometer" is a gravity indentation device which utilizes a blunt, weighted pin which rests against the eyeball. As the pin deforms the eye's surface, a linkage attached to the pin causes a pointer to move along a calibrated numerical scale, permitting the indicated intraocular pressure to be read from the scale.

The so-called "Applanation tonometer" is widely employed today and utilizes a small flat lens having a circle inscribed on its surface. This lens is placed against the surface of the eye and force is increasingly applied to deform the eye until the area of the eye surface thereby flattened against the flat lens matches the area of the inserted circle on the lens, whereupon the force is then read from a scale which is calibrated to the intraocular pressure.

In the so-called "air-test tonometer", a puff of air of a known volume and pressure is applied against the surface of the eye, while sensors detect the amount of deformation in the eye's surface caused by application of the puff of air. Such a device is described for example in U.S. Pat. No. 3,545,260.

The so-called "MacKay-Marg tonometer" is an applanation-type device in which a sensor is bounced off the cornea and the intraocular pressure is recorded graphically on a chart.

A common disadvantage of the currently used devices is that a physician and/or assistant is required to be in attendance during the testing procedure. In some cases, it is also necessary to medicate or topically anesthetize the patient's eye prior to testing. Thus, with the devices currently employed no practical means has been provided for measuring a patient's intraocular pressure around the clock and over an extended period of time, and without the attendance of a physician or technician. Consequently, with the currently available devices, the conventional practice is to routinely check a patient's intraocular pressure, for example at intervals of from two weeks to six months, and in such cases the intraocular pressure is only tested for a brief period of a few seconds at a time. Thus, the current testing practices are rather crude in that there is little assurance of an accurate reading being obtained during such a brief testing period, given the variations and fluctuations in intraocular pressures over a diurnal or longer period which cannot be practically monitored with the currently used testing devices and methods. Therefore, it may not be possible to reliably determine whether or not a patient's intraocular pressure is under control, nor to determine the proper treatment, nor to assess whether or not the patient may go blind.

Thus, there is presently a great need for a means for accurately monitoring a patient's intraocular pressure on an extended basis, such as over a period of 24 hours or longer. It is also desirable to monitor a patient's intraocular pressure under normal living conditions, and without the need for anesthesia or other drugs. It is further desirable to be able to monitor a patient's intraocular pressure without the constant attendance of a physician or technician. Still further, it is highly desirable to be able to monitor a patient's intraocular pressure outside the doctor's office or hospital and under various living conditions, such as while the patient is sleeping, exercising, relaxing, straining, at different altitudes, while under stress, etc.

The present invention is directed to meeting the above-mentioned needs as well as to overcoming the problems and disadvantages inherent in current devices and methods.

The intraocular pressure sensor of the present invention utilizes a small piezo-electric strain gauge for directly monitoring intraocular pressure. The piezo-electric strain gauge is mounted in a small holder which is shaped similar to a contact lens. The sensor is intended to be placed in contact with the sclerotic portion of the eyeball (sclera), that is, so that the sensor presses on the white part of the eye. The sensor is held in position against the eyeball by the eyelid as well as by the suction effect of the shaped holder. By making the sensor small, it is possible to place the sensor in the lower cul-de-sac of the eye behind the lower eyelid. Wire leads from the strain gauge are passed through the holder and along and out over the lower eyelid, and these wire leads may be connected to a suitable power source and monitoring/recording circuitry for receiving the sensor output signal and converting the output signal into a pressure value.

It is known to use piezo-electric and other devices for remotely monitoring bodily pressures. For example, U.S. Pat. No. 3,239,696 discloses a piezo-electric pressure transducer for measuring cardiovascular circulatory system pressure in the human body. U.S. Pat. No. 4,023,562 discloses a miniature piezo-resistive transducer device adapted to be implanted within the body for directly monitoring internal fluid or pneumatic pressures therein, utilizing semiconductor strain gauge elements including a piezo-resistive bridge.

U.S. Pat. No. 3,948,248 describes placing a piezo-resistive weight on the corneal surface to record intraocular pressures, in connection with the ultrasonic detection of intraocular pressures. In U.S. Pat. No. 3,903,871 there is disclosed a portable compression-type opthalmodynamometer for determining retinal artery pressures, while in U.S. Pat. No. 4,281,662 there is disclosed a microprocessor-controlled device which stores the magnitude value data of systolic and diastolic pressures and calculates the percentage difference therebetween. Also disclosed are a display and bar graph as well as a strip chart recorder.

However, the known devices fail to offer a suitable sensor for monitoring intraocular pressure which can provide accurate intraocular pressure readings over an extended period while worn in the eye under various living conditions.

It is therefore an object of the present invention to provide an intraocular pressure sensor which enables the intraocular pressure to be accurately monitored on an extended basis over a long period of time.

It is also an object of the present invention to provide an intraocular pressure sensor which permits the intraocular pressure to be monitored under normal living conditions.

It is additionally an object of the present invention to provide an intraocular pressure sensor which permits intraocular pressures to be monitored without a doctor or technician in attendance.

It is further an object of the present invention to provide an intraocular pressure sensor which can be worn in the eye like a contact lens.

It is still further an object of the present invention to provide an intraocular pressure sensor which permits a patient's intraocular pressure to be tested without the necessity for administering medication or anethesia.

BRIEF DESCRIPTION OF THE DRAWINGS

These and other objects, features and advantages of the present invention will be more fully appreciated from the following detailed description taken together with the drawings in which FIG. 1 is a plan view showing the intraocular pressure sensor according to the present invention.

FIG. 2 is a cross-sectional view of the intraocular pressure sensor of the present invention taken along line II—II in FIG. 1.

FIG. 3 is a perspective view showing the intraocular pressure sensor of the present invention in position, worn in the eye.

DETAILED DESCRIPTION OF THE INVENTION

Referring now to the drawings figures in which like reference numerals designate like elements, there is shown in FIGS. 1 and 2 the intraocular pressure sensor of the present invention designated generally at 10. A semi-rigid circular holder 12 is formed in the shape of a contact lens with a concave inner surface 12a and a convex outer surface 12b in order to give the holder 12 a curved cross-section as shown in FIG. 2. Holder 12 may have a diameter of 11 millimeters with the inner surface 12a being curved with a radius of 12 millimeters. The outer surface 12b is given a slightly smaller radius than inner surface 12a in order to give holder 12 a thick center portion 12c which tapers gradually outwardly towards the outer peripheral edge 12d.

In the center portion 12c of holder 12 there is formed a circular recess 12e which opens into inner surface 12a. Into recess 12e there is suitably bonded a pressure transducer 14 with its pressure sensitive surface 14a protruding slightly above the inner surface 12a so as to be inside the radius of curved inner surface 12a by 0.025 to 0.05 millimeters.

A hole 16 is formed in holder 12 from inner surface 12a proximate central recess 12e and leading out to outer surface 12b. Fine wire leads 18 from pressure transducer 14 are led out through this hole 16, and wire leads 18 may be suitably terminated at an adequate length for connection to an external device (not shown).

A thin layer 20 of silicon rubber compound or other suitable flexible material is applied to the exposed sensitive surface 14a of pressure transducer 14. Layer 20 extends outwardly of transducer 14 onto inner surface 12a of holder 12, thus defining a smooth central pad on the inner surface of sensor 10. Layer 20 protects the eye and also insulates and waterproofs pressure transducer 14.

A suitable commercially available low profile pressure transducer which may be used in the present invention is the model no. 8515a15a from Endevco Corporation of San Juan Capistrano, Calif. This piezo-type pressure transducer has a diameter of 6.3 millimeters and a thickness of 0.63 millimeter. Holder 12 may be formed of polymethylmethacrylate or other suitable semi-rigid material, and can be fashioned in a manner similar to that for a corneal contact lens.

The sensor 10 of the present invention may be advantageously worn in the eye in similar manner to a so-called "hard" contact lens, but whereas contact lenses for vision correction are intended to be worn centered over the cornea, the sensor 10 of the present invention is intended to be placed against the sclera of the eyeball, preferably in the location of the lower cul-de-sac between the lower eyelid and eyeball as shown in FIG. 3. Because of its thin profile and small diameter the sensor 10 may be worn for extended periods such as for 24 hours.

Due to the nature and curvature of holder 12 a slight suction results between the curved inner side of the sensor 10 and the eyeball surface which assists in holding the sensor 10 in position. The pressure of the inner surface of the lower eyelid against the outer surface 12b of holder 12 also assists in holding the sensor 10 in position pressed against the sclera.

The sclera is preferable as a sensing site because it is less sensitive and less susceptible to injury than the cornea. There are also theoretical advantages in checking the intraocular pressures on the sclera as opposed to checking pressures on the cornea.

The pressure transducer 14 is preferably a strain gauge in the form of a thin, resistive Wheatstone bridge configuration and planar in shape. Any suitable transducer devices may be used, so long as they are responsive to deflection forces applied perpendicularly to the planar sensing surface of the transducer.

The sensitive area 14a of the transducer 14 must be in contact with the eye, but should not be held against the eye with such pressure that the reading obtained would be at or near a maximum value. Therefore, transducer 14 should be mounted in holder 12 such that an arc drawn from one edge of holder 12 to sensitive surface 14a and to the diametrically opposite edge of holder 12 will match the arc of the surface of the eye at the sensing location. By forming the holder 10 with a suitable curvature and mounting the pressure transducer 14 with its sensitive surface 14a protruding from the holder inner surface 12a by 0.025–0.05 mm, the planar sensitive surface 14a of the pressure transducer 14 will make contact with the curved eyeball so that the intraocular pressure inside the eye will affect the pressure transducer's sensing elements 14b, 14c.

Wire leads 18 are of fine insulated flexible wire and of sufficient length as to permit the wire leads 18 to be led out over the lower eyelid and connected to a suitable recording device (not shown) for supplying power to and receiving output signals from pressure transducer 14. Wire leads 18 are preferably formed very finely so as to be able to be led out at the corner of the eye between the upper and lower eyelids. In this way, the sensor 10 can be worn in the eye with the eyelids shut, as when sleeping, and without hindering the natural blinking movement of the eyelids and normal orbital movements of the eyeball.

Wire leads 18 will preferably be connected to a recording device having provisions for supplying a constant voltage to transducer 14 (if a bridge-type strain gauge is used as the pressure transducer), and for recording and/or displaying pressure readings detected by transducer 14. Pressure readings could thus be taken continuously, or at periodic intervals of, for example, every fifteen minutes, on an extended basis in order to track the fluctuations and diurnal variations in the intraocular pressures. Recording devices for this purpose would also preferably be small and portable so as permit wearing by the patient, while also permitting storage of readings for later monitoring and printing out at a doctor's office. Recording devices of this type utilizing microprocessor control and digital conversion and storage are within the ordinary skill in the art and do not form a part of the present invention.

The sensor 10 of the present invention can be used for monitoring a patient's intraocular pressures, and then reused on another patient after appropriate sterilization. Testing can be performed on a patient at one time, and then later on a week, month or year later without adverse effects, in order to evaluate the efficacy of treatment or to monitor the patient for increasing intraocular pressures. Because the sensor 10 is worn in the patient's eye like a contact lens, the sensor 10 may be comfortably worn on an extended basis outside the doctor's office or hospital and under various living conditions such as while sleeping, exercising, relaxing, straining, at different altitudes, under stress, etc., with the intraocular pressure being accurately detected throughout the day and night, thus providing a clear picture to the practitioner of the patient's intraocular pressure condition. Because the sensor 10 may be comfortably worn, it is not necessary to medicate or anesthetize the eye prior to testing the intraocular pressure. Further, when the sensor 10 is used with a portable battery-powered recording device, it is not necessary for a physician or technician to be in attendance during testing. Thus, the device can be calibrated in the doctor's office after the sensor is positioned in the eye, and the patient can then carry on normal activities outside the doctor's office while monitoring continues, only returning at the appropriate time to the doctor's office after the testing period has been completed.

It will be appreciated that the intraocular pressure sensor of the present invention described above is amenable to various modifications within the scope of the invention. For example, the configurations of the holder and transducer may be appropriately modified for eyes of different size and curvature. It is therefore intended that the scope of the present invention be limited only by the appended claims.

What is claimed is:

1. An intraocular pressure sensor, comprising:
   curved holder means adapted to conform to the curvature of the eyeball for holding said sensor in contacting position with the surface of the eye, the holder means having a circular configuration with a concave inner surface conforming to the surface of the eye and a convex outer surface, the holder means being outwardly tapered in cross-section from a center portion thereof toward an outer peripheral edge thereof, a recess being formed in said center portion and opening to said concave inner surface;
   pressure transducer means for detecting intraocular pressure and for providing an output signal corresponding thereto, said pressure transducer means having a planar pressure sensitive surface and being mounted in said central recess in said holder means such that an arc drawn from one peripheral edge of the holder means to the pressure sensitive surface of the pressure transducer means and to the diametrically opposite peripheral edge of the holder means matches the arc of the surface of the eye at which the intraocular pressure is to be sensed, whereby suction results between the concave inner surface of the holder means and the surface of the eye for holding the pressure sensitive surface of said pressure transducer means in pressure-sensing contact with the surface of the eye; and
   wire leads operably connected to said pressure transducer means for supplying power thereto and for transmitting output signals therefrom.

2. An intraocular pressure sensor according to claim 1, further comprising a thin layer of flexible material covering at least the pressure sensitive surface of said pressure transducer means.

3. An intraocular pressure sensor according to claim 1, wherein said pressure sensitive surface of said pressure transducer means protrudes above the inner concave surface of said holder means.

4. An intraocular pressure sensor according to claim 1, wherein said holder means is provided with a hold therethrough for leading out said wire leads from said pressure transducer means to said outer convex surface of said holder means.

5. An intraocular pressure sensor according to claim 1 wherein said holder means is formed of polymethylmethacrylate.

6. An intraocular pressure sensor according to claim 1, wherein the holder means has a diameter of 11 mm, the concave inner surface of said holder means is formed with a radius of 12 mm, and the pressure sensitive surface of the pressure transducer means protrudes above said concave inner surface by a distance of 0.025 to 0.05 mm.

7. An intraocular pressure sensor according to claim 1 wherein said pressure transducer means is a piezoresistive Wheatstone bridge strain gauge.

8. An intraocular pressure sensor according to claim 1, wherein said holder means is semi-rigid.

* * * * *